United States Patent [19]

Tanaka

[11] 4,206,547
[45] Jun. 10, 1980

[54] DENTAL INSTRUMENT

[76] Inventor: Asami Tanaka, 9307 North Lavergne, Skokie, Ill. 60077

[21] Appl. No.: 946,878

[22] Filed: Sep. 29, 1978

[51] Int. Cl.² ............................................. A61C 3/08
[52] U.S. Cl. .................................... 433/141; 433/150
[58] Field of Search ................. 32/40 R, 51, 66, 60, 32/41

[56] References Cited

U.S. PATENT DOCUMENTS

| 3,727,314 | 4/1973 | De Angeles | 32/41 |
| 4,060,897 | 12/1977 | Greenstein | 32/40 R |

OTHER PUBLICATIONS

Silverman's Supply Catalogue 1976 edition p. 11, Apollo Road Plymouth Meeting, Pa. 19462.

Primary Examiner—Robert Peshock
Attorney, Agent, or Firm—Neuman, Williams, Anderson & Olson

[57] ABSTRACT

This invention relates generally to an instrument used in making dental restoratives and more particularly concerns a unitary instrument used to perform the functions of mixing and applying porcelain paste to a metal understructure utilized in the dental restorative and for condensing the porcelain paste subsequent to being applied to the understructure.

5 Claims, 4 Drawing Figures

DENTAL INSTRUMENT

BACKGROUND OF THE INVENTION

The fabrication of a dental restorative, such as a crown or bridge, normally involves building up porcelain or a similar material on a metallic understructure, the latter being necessary to provide strength to the crown or bridge. The porcelain is applied as a wet paste and generally consists of a mixture of porcelain powder and a wetting agent, for example, water. It is necessary to use a paste so that the porcelain can be readily contoured into a toothlike shape. The paste is formed by mixing and stirring the powder and wetting agent in any convenient vessel. The paste after being properly mixed, is transferred by a suitable device (e.g., spatula) from the vessel to the exposed surface of the metallic understructure.

Irregularities in the porcelain can weaken the crown or bridge and cause cracks or other surface imperfections to result. These irregularities may occur due to lumps within the paste or from moisture or air entrapped in the porcelain paste. Furthermore, voids caused by the entrained moisture or air can result in excessive shrinking of the porcelain when it is fired. The paste lumps can be eliminated by more thorough and effective mixing with a spatula or other suitable device.

Conventionally, the voids are eliminated during buildup and shaping of paste on the understructure by a technique known as condensation of the porcelain paste. This technique causes compaction of the porcelain paste on the understructure whereby the entrapped moisture and air percolate to the exposed surface of the applied paste and thus increases the concentration of porcelain powder on the understructure. The condensation technique is normally achieved by vibrating the applied porcelain paste on the understructure.

The porcelain paste is applied to and shaped on the understructure while the latter is supported on a plaster mold of the jaw. It is extremely desirable to condense the paste at this stage while it is being applied and shaped. If condensation is postponed until after the paste is shaped, the settled and compacted porcelain may require major reshaping. However, it has been found that condensation induced by a vibration action at an early stage eliminates an excessive amount of moisture and, thus, prevents proper shaping of the porcelain. Heretofore, the condensation step was normally postponed until the shaping was completed or was limited to tapping the entire plaster mold against the bench top. Such a procedure, however, was time consuming and awkward. In lieu of tapping the whole mold on a bench, effective condensation can be accomplished by utilizing a small mallet; such mallet tapping causes a substantially less severe and more easily controllable condensation of the porcelain. Typically, the dental technologist alternates frequently between applying, shaping, and condensing the porcelain paste on the understructure.

When the porcelain paste has attained the desired shape, the understructure with shaped porcelain thereon is transferred from the plaster mold to a clamp-like holder such as forceps. Generally, condensation is initiated at this point by rubbing a ribbed tool against a portion of the clamp-like device holding the understructure. The paste previously applied to the understructure is not sufficiently hard at this time for the tool to tap the paste directly.

The fabrication of a dental crown or bridge requires the dental technologist's close attention to small details. The frequent alternation between applying and condensing the porcelain paste is particularly demanding on the technologist and conventionally requires the use of different instruments to perform each function and even tapping the plaster mold against a bench top. The need to put one instrument down and then find and pick up a second instrument in rapid succession is difficult and time consuming and often leads to error.

SUMMARY OF THE INVENTION

Accordingly, it is a general object of the present invention to provide a single instrument which is readily adapted to perform multiple operations during the manufacture of a dental restorative, such as mixing, applying and condensing porcelain paste or the like on a metallic understructure.

Another object is to provide an instrument which is adapted to readily induce different types of condensation of the porcelain paste during various stages in the manufacture of a dental restorative.

other objects and advantages of the invention will become apparent upon reading the following detailed description and appended claims and upon reference to the accompanying drawings.

In accordance with one embodiment of the invention, an improved unitary instrument is provided for use in mixing, applying and condensing a porcelain paste during the manufacture of a dental restorative, such as a crown or bridge. The instrument includes an elongated handle; first means on the handle for mixing and applying the paste to the understructure; second means on the handle and longitudinally spaced from said first means for imparting a tapping force to the porcelain paste applied to the understructure; and third means on the handle and intermediate said first and second means for imparting vibration to the applied porcelain paste. The three means are located on the handle to facilitate sequential use thereof during manufacture of a dental restorative.

DESCRIPTION

For a more complete understanding of this invention, reference should now be made to the embodiment illustrated in greater detail in the accompanying drawings and described below by way of an example of the invention. In the drawings.

It should be understood, of course, that the invention is not necessarily limited to the particular embodiment illustrated herein.

Figure 1:
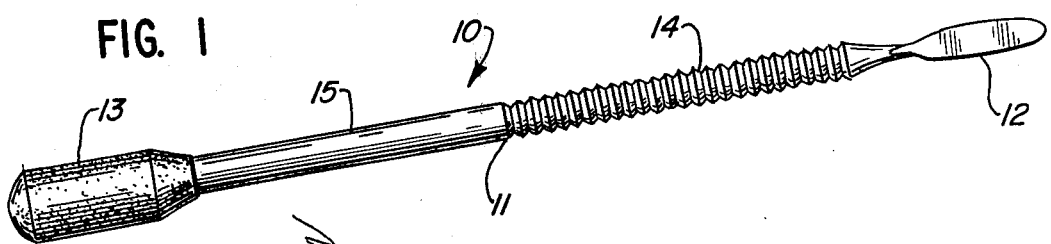
FIG. 1 is a perspective view of one embodiment of the improved instrument.

Referring now to the drawings, and more particularly to FIG. 1, one form of the instrument 10 is shown which is adapted to be utilized during the manufacture of a dental restorative D, such as a crown or bridge. The instrument includes an eongated rod-like handle 11 preferably of a rigid metallic material and having one end thereof flattened so as to form a spatula blade 12. The function of blade 12 will be described more fully hereinafter. The opposite end of handle 11 has affixed thereto an enlarged mallet member 13. Disposed intermediate blade 12 and mallet member 13 is an elongated serrated or roughened segment 14. The length of segment 14 may vary but preferably it is approximately one-half the distance between blade 12 and mallet member 13. The member 13 has an exterior surface of a plastic material (e.g., Teflon) which will not cause the applied porcelain or plaster mold to be scarred or scuffed when being tapped thereby during one stage of the manufacturing process. The mallet member 13 may be a separate piece affixed to the end of the handle or it may be integral with and of the same material as the remainder of the instrument. In the latter situation, a suitable plastic coating would be applied to the exterior surface of the member.

The segment 15 of the handle intermediate the mallet member 13 and segment 14 is shaped so that it may be conveniently and comfortably grasped by the fingers and thumb of one hand of the person making the dental restorative D. The overall length of the instrument 10 may vary but preferably is within a range of about 6 to about 12 inches.

The manufacturing of a dental crown, for example, involves first that a plaster mold 16 be made of the patient's jaw section in which the crown D is to be located. The natural tooth in question, which is to be crowned, is ground so that the surface thereof facing the other jaw section is substantially flat and recessed relative to the adjoining teeth and thereby provides a base upon which the crown is to be eventually attached. The impression, from which the plaster mold is made, is taken after the natural tooth has been properly ground to form the desired base. Thus, the plaster mold will duplicate the tooth base to which the crown is to be attached.

The crown D itself includes an understructure preferably of metal (e.g., a precious metal alloy) which is malleable so that it will conform substantially to the flat base surface and also have a peripheral flange which will encompass the portion of the natural tooth circumjacent the flat base surface. In some instances a peg or pintle, not shown, may be positioned centrally of the flat base surface so as to provide a more secure anchoring of the crown to the tooth base.

Figure 2:
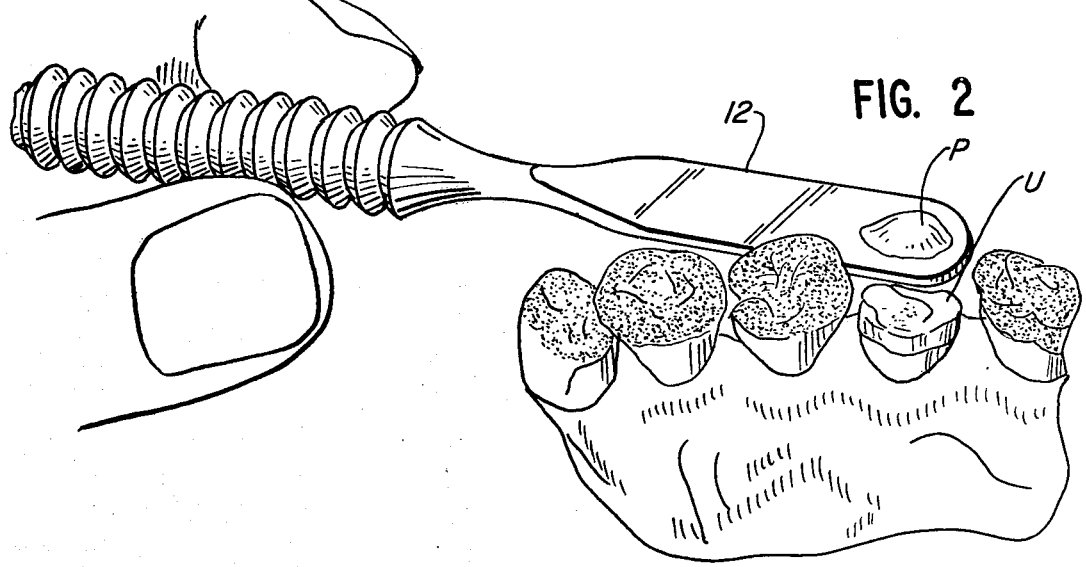
FIG. 2 is an enlarged fragmentary perspective view showing one end of the instrument of FIG. 1 in the act of applying a porcelain paste to an understructure disposed on a plaster mold during one stage of manufacturing the dental restorative.
Figure 3:
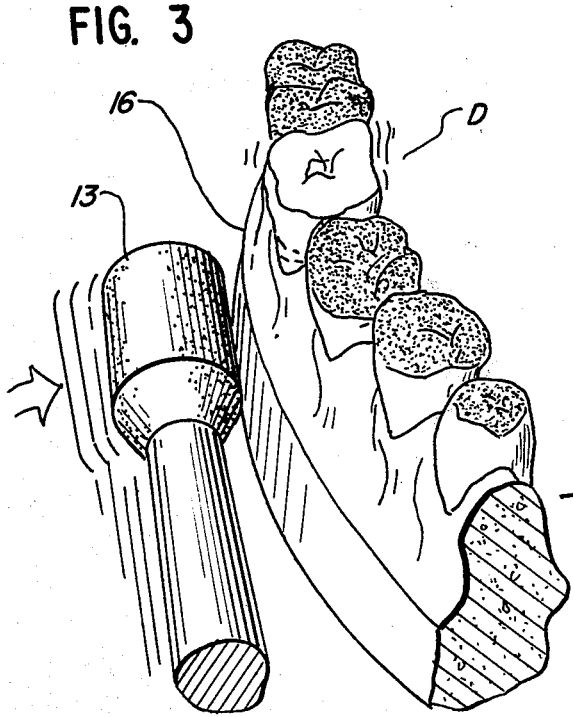
FIG. 3 is similar to FIG. 2 but showing the opposite end of the instrument of FIG. 1 imparting a tapping action to the plaster mold in the vicinity of the dental restorative to effect initial condensation of the applied porcelain paste and while the understructure is still mounted on the plaster mold.

Shaping of the understructure is normally performed on the plaster mold and then, while the understructure remains in place on the tooth base of the mold, porcelain paste is built up in a conventional manner on the understructure so as to duplicate the shape of the natural tooth which was removed by grinding. It is during such buildup that the spatula blade 12 of the instrument 10 is utilized. The width of blade 12 is narrow (e.g., 5/32") so that it will conveniently fit between the teeth adjoining the tooth being crowned. The width of the blade may vary depending upon the location in the jaws of the tooth being crowned and the physical dimension of the jaws itself. As seen in FIG. 2, the blade 12 is adapted to apply small portions of the porcelain paste P onto the understructure U until the paste accumulated thereon has attained the desired height. During the build-up of the paste, the dental technician or person manufacturing the crown, will turn the instrument around and cause the mallet member 13 to gently tap repeatedly the side of the mold 16, as seen in FIG. 3. As the mold is being gently tapped, partial condensation of the porcelain paste will occur causing air and moisture entrapped within the paste to percolate to the exposed surface and evaporate or be removed by any suitable means.

Figure 4:
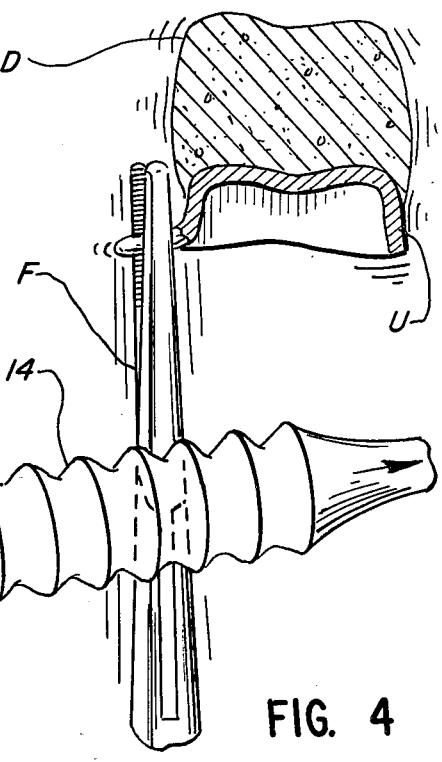
FIG. 4 is an enlarged fragmentary perspective view of the instrument of FIG. 1 showing the dental restorative removed from the plaster mold and being held by forceps while the latter is moved back and forth across an elongated serrated portion of the handle so as to impart vibration to the forceps and effect final condensation of the porcelain forming the restorative.

Once the desired build-up of the paste has been achieved, the blade 12 will be utilized to properly contour the crown. The crown and understructure are then removed as a unit from the mold and firmly held by forceps F, as seen in FIG 4. While the forceps are grasping a portion of the understructure, the jaws of the forceps are manually moved back and forth across the serrated segment 14 of the instrument 10 causing the crown to vibrate and resulting in final condensation of the porcelain paste. The vibrated crown is then heated so as to cause hardening of the porcelain paste. The crown is then placed in position on the base portion of the material and secured thereto by a suitable epoxy or cement.

It has been found that a crown made in the manner above described is highly resistant to cracking or fracturing and will remain firmly in place. The improved instrument enables the aforedescribed manufacturing steps to be readily carried out in facile expeditious way. It avoids the necessity of utilizing a variety of instruments to carry out the steps.

I claim:

1. A unitary instrument for use in making a dental restorative having an understructure and a buildup of porcelain thereon, and for regulating condensation of the porcelain during buildup, said instrument comprising an elongated handle; a narrow blade-like member affixed to said handle and protruding therefrom to be manipulated to effect a predetermined buildup of a porcelain paste on a supported understructure; and a mallet member affixed to said handle and spaced longitudinally from said blade-like member; said mallet member being a mass of substantially cylindrical configuration and having its longitudinal axis the same as the longitudinal axis of said handle and of a radius grater than said handle and being adapted to impart intermittently a tapping force to effect a vibratory action to the supported understructure during buildup of the porcelain paste thereon to induce a rate of condensation of the porcelain paste according to the stage in the buildup procedure; said handle being provided with an elongated roughened segment disposed intermediate said blade-like member and said mallet member, said roughened segment being adapted to impart vibrations to the supported understructure interchangeable with said mallet member subsequent to the predetermined buildup of the porcelain paste and upon the segment and the supported understructure being in contact and removable relative to one another longitudinally of the segment.

2. The instrument of claim 1 wherein said members are integral with said handle.

3. The instrument of claim 1 wherein the mallet member has an exterior surface of scuff-proof material.

4. The instrument of claim 3 wherein the scuffproof material is teflon.

5. The instrument of claim 1 wherein the roughened segment of the handle includes a plurality of annular serrations.

* * * * *

UNITED STATES PATENT AND TRADEMARK OFFICE
CERTIFICATE OF CORRECTION

PATENT NO.  : 4,206,547
DATED       : JUNE 10, 1980
INVENTOR(S) : ASAMI TANAKA

It is certified that error appears in the above-identified patent and that said Letters Patent are hereby corrected as shown below:

Column 2, line 23 - "other" should be  --Other--

Column 3, line 8 - "eongated" should be  --elongated--

Claim 1, column 4, line 44 - "grater" should be  --greater--

Signed and Sealed this

Twelfth Day of August 1980

[SEAL]

Attest:

SIDNEY A. DIAMOND

Attesting Officer

Commissioner of Patents and Trademarks